US 6,623,477 B1

(12) United States Patent
Elbrecht et al.

(10) Patent No.: US 6,623,477 B1
(45) Date of Patent: Sep. 23, 2003

(54) MEDICAL INSTRUMENT FOR PHACOEMULSIFICATION

(75) Inventors: Jens Elbrecht, Jena (DE); Eckhard Schroeder, Eckental (DE); Frank Weidner, Loeberschuetz (DE)

(73) Assignee: Asclepion-Meditec AG, Jena (DE)

( * ) Notice: Subject to any disclaimer, the term of this patent is extended or adjusted under 35 U.S.C. 154(b) by 0 days.

(21) Appl. No.: 09/831,130

(22) PCT Filed: Nov. 5, 1999

(86) PCT No.: PCT/EP99/08472

§ 371 (c)(1),
(2), (4) Date: Oct. 1, 2001

(87) PCT Pub. No.: WO00/27325

PCT Pub. Date: May 18, 2000

(30) Foreign Application Priority Data

Nov. 6, 1998 (DE) .......................... 198 52 574

(51) Int. Cl.⁷ ............................................. A61B 18/18
(52) U.S. Cl. ................. 606/6; 606/4; 606/13; 606/16
(58) Field of Search .............................. 606/4–6, 13–16

(56) References Cited

U.S. PATENT DOCUMENTS

| 3,844,272 A | 10/1974 | Banko | |
| 4,002,169 A | 1/1977 | Cupler et al. | |
| 4,559,942 A | * 12/1985 | Eisenberg | ................ 128/303.1 |
| 4,744,360 A | * 5/1988 | Bath | ........................ 128/303.1 |
| 4,825,865 A | * 5/1989 | Zelman | .................... 128/303.1 |
| 5,123,902 A | * 6/1992 | Muller et al. | .................. 604/21 |
| 5,257,988 A | 11/1993 | L'Esperance, Jr. | |
| 5,730,156 A | * 3/1998 | Mackool | ................. 128/898 |
| 5,738,677 A | * 4/1998 | Colvard et al. | ................. 606/4 |
| 6,322,557 B1 | * 11/2001 | Nikolaevich et al. | .......... 606/6 |

FOREIGN PATENT DOCUMENTS

| DE | 38 22 011 | 1/1990 |
| WO | WO 93/20895 | 10/1993 |

* cited by examiner

Primary Examiner—Linda C. M. Dvorak
Assistant Examiner—Ahmed M Farah
(74) Attorney, Agent, or Firm—Reed Smith LLP

(57) ABSTRACT

A medical instrument for phacoemulsification with which the biological tissue of a lens of the eye is comminuted by the introduction of energy, the comminuted product is sucked out through an incision in the cornea, while intraocular pressure is maintained by supplying an irrigating liquid. In an instrument of the type mentioned above, two cannulas are provided for sucking out the ablated lens material and for supplying the irrigating liquid and are connected, via feed lines, with the suction device and with the supply device. A switchable directional valve is provided in the feed lines between the cannulas and the suction device and supply device, by means of which, in a first valve position, a first cannula is connected with the suction device and the second cannula is connected with the supply device and, in a second valve position, the second cannula is connected with the suction device and the first cannula is connected with the supply device.

20 Claims, 4 Drawing Sheets

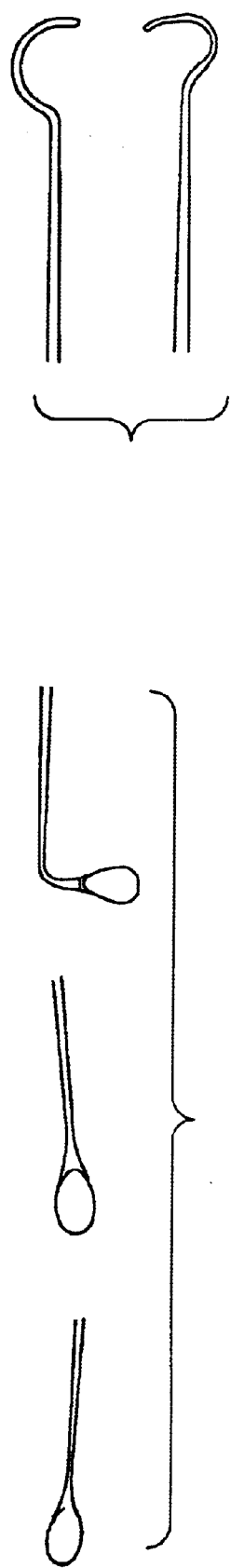
FIG. 4A
FIG. 4B
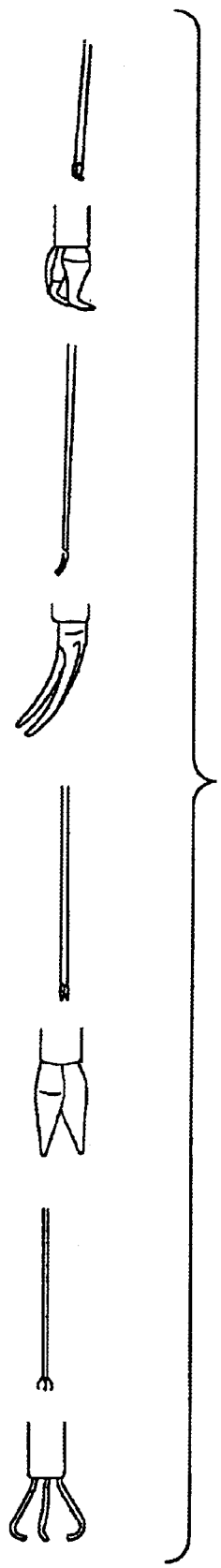
FIG. 4C

MEDICAL INSTRUMENT FOR PHACOEMULSIFICATION

BACKGROUND OF THE INVENTION

1. Field of the Invention

The invention is directed to a medical instrument for phacoemulsification with which the biological tissue of a lens of the eye is comminuted by the introduction of energy, the comminuted product is sucked out through an incision in the cornea, while intraocular pressure is maintained by supplying an irrigating liquid.

2. Discussion of the Relevant Art

For purposes of carrying out the above-mentioned operation, the known prior-art instruments have a supply cannula for the irrigating liquid and a suction cannula for the core and core fragments. In conventional methods for phacoemulsification, a cannula is inserted into the eye to suck out the cataractous lens core in its entirety. However, this method, known since 1967, can be advantageously applied only for soft lenses.

With hard cores, the lens material is first comminuted by supplying energy, preferably via ultrasound or laser, and the small fragments are then sucked out through the suction cannula which is enclosed by a handpiece. The volume of liquid and lens fragments sucked out of the anterior chamber is compensated by an infusion of rinsing liquid into the anterior chamber via the supply cannula, so that intraocular pressure is substantially maintained.

The supply of liquid, known as irrigation, is carried out in all known handpieces via a supply cannula which is constructed as a sleeve that is fitted over the suction cannula. During the operation, the liquid flows between the suction cannula and the inner wall of the sleeve to the distal end of the handpiece, where two outlet openings are generally provided The introduction of energy is currently carried out by ultrasound in more than 90% of cataract extractions. It is disadvantageous that the introduction of ultrasound into the tissue involves unwanted generation of heat, so that cooling must be carried out in order to prevent damage to healthy tissue. To this extent, the sleeve serves a dual function in ultrasound phacoemulsification in that the liquid flowing between the suction cannula and inner wall of the sleeve is utilized for cooling at the same time. For this reason, handpieces for phacoemulsification using ultrasound technology are, in principle, constructed only with integrated supply cannula, suction cannula and integrated ultrasound conductor.

Because of the need to supply liquid and the formation of the sleeve as a cooling element, the distal end of the handpiece is necessarily relatively large. Accordingly, the suction cannula, for example, which itself has a diameter in the range of 0.8 mm to 1.3 mm, is enlarged to a diameter of about 2.5 mm through the use of the sleeve which is drawn over it. In order to introduce a cannula with these dimensions into the tissue, an incision on the order of 3 mm to 3.2 mm is necessary.

However, large incisions of this kind result in loss of aqueous humor and rinsing solution during the operation. Further, the risk of astigmatism induced by the operation increases as the size of the incision increases. Visual rehabilitation also progresses relatively slowly with incisions of this size compared to smaller incisions.

For this reason, medical efforts are directed to increasingly smaller incisions with the purpose of introducing injectable lenses into the anterior chamber through these small incisions. However, it is necessary for this purpose that the comminuted lens material can be sucked out through small incisions and that irrigating liquid can be supplied through the same.

Further, laser phacoemulsification is known from the prior art in which energy is introduced via laser radiation which is aimed directly on the tissue to be comminuted. A laser wavelength with a very small depth of penetration into the aqueous matter in the interior of the eye must be selected; wavelengths in the low UV range and infrared range are suited to this purpose. In this connection, the use of Er:YAG lasers with a wavelength of $\lambda=2.9$ $\mu$m has proved successful. In this way, a quasi-nonthermal introduction of energy is achieved and the problems arising from the use of ultrasound with respect to heat generation no longer occur.

However, the handpieces known from the prior art for laser phacoemulsification likewise have the disadvantage that the supply cannula, suction cannula and energy supply (for example, via light-conducting fibers) are integrated in a handpiece and the outlets are spatially oriented to a common area. This also requires a large incision through which the supply of irrigating liquid and laser energy and the aspiration of comminuted core material must be carried out.

OBJECT AND SUMMARY OF THE INVENTION

On this basis, it is the primary object of the invention to provide a medical instrument for phacoemulsification by which it is possible to replace the lens through small incisions in the cornea while maintaining the advantageous quasinonthermal introduction of energy.

According to the invention, this object is met in a medical instrument for phacoemulsification with which the biologcal tissue of a lens of the eye is ablated by the introduction of energy, the ablated product is sucked out through an incision in the cornea and the intraocular pressure is maintained by supplying an irrigating liquid. The instrument comprises two cannulas for sucking out the ablated lens material and for supplying the irrigating liquid. At least one device is provided for the introduction of energy through laser radiation. The two cannulas are enclosed by separate handpieces which are movable relative to one another. One of the handpieces with the first cannula communicates with a suction device via a feed line. The other of the handpieces with the second cannular communicates with a supply device for the irrigating liquid via another feed line.

With the medical instrument suggested according to the invention, it is possible to carry out phacoemulsification through small incisions resulting essentially in the advantages that the risk of inducing astigmatism is now only slight, a quicker postoperative visual rehabilitation is also possible and a lens can now be introduced into the eye through injection in an accessible phacoemulsification technique.

In this connection, a highly preferred application of the instrument suggested according to the invention consists in that after the comminuted core material is sucked out via one of the two handpieces or via the cannula integrated in the respective handpiece, the substance is injected, remains in the eye and replaces the old eye lens.

For this purpose, in constructional variants of the invention, the handpieces or the cannula are outfitted with connections for corresponding instruments for introducing a substance of this kind, e.g., for injection or the like.

In another preferred constructional variant, each of the two handpieces is provided for sucking out the comminuted core material and for supplying rinsing liquid. For example, when the cannulas of both handpieces are displaced with their distal end from opposite sides toward the lens of the eye, it is possible in this way to carry out the comminution of tissue as well as aspiration of the ablated products selectively and alternately in both of these opposite positions.

Compared with one-sided aspiration, this has the advantage that the cannula need not be introduced as deeply, which in turn fits in with the striving for small incisions and gentle treatment of tissue. For this purpose, both handpieces are connected, via transport lines or feed lines, to a switchable directional valve by means of which the flow directions can be reversed when sucking out the ablated product and when supplying the rinsing liquid. This switching can be carried out advantageously with a foot switch.

In this connection, it can further be provided that both handpieces are outfitted with fiber tips for supplying laser energy. The fiber tips can preferably be arranged inside the cannula and can also be arranged so as to be displaceable inside the cannula in the radiating direction of the laser energy and in the flow direction. This results in the advantage that the fiber tip can then be retracted from the treatment site, for example, when no laser energy is being radiated during irrigation. The outlet end of the respective cannula, in contrast to the fiber tip, remains directly at the treatment site.

In another very preferred construction of the invention, it is provided that a device for eliminating clogging within the cannula or within the feed lines is associated with one or both of the handpieces. This device can have, for example, a cleaning element which can be inserted laterally into the cannula and/or into one of the feed lines and which is displaceable within the respective line cross section. This cleaning element can be, for example, a flexible rod outfitted with a thickened end or a cleaning spiral whose diameters are adapted to the line cross section.

Another advantageous construction consists in that one or both of the handpieces is/are outfitted with auxiliary instruments for holding, gripping, turning, pushing, cutting, splitting, protecting and/or illuminating the tissue at the treatment site. These auxiliary elements are preferably interchangeable and can be connected with the respective handpiece, for example, via an attaching mechanism. In this connection, further constructions are possible in which the auxiliary instruments can be retracted into the handpiece via a displacing mechanism or are arranged so as to be displaceable on the outside of the handpiece, so that they can be moved into the appropriate use position, as needed, at any time.

BRIEF DESCRIPTION OF THE DRAWINGS

The invention will be explained more fully in the following with reference to two embodiment examples. The accompanying drawings show:

FIGS. 4a–4c a selection of auxiliary instruments.

DESCRIPTION OF THE PREFERRED EMBODIMENTS

Figure 1:
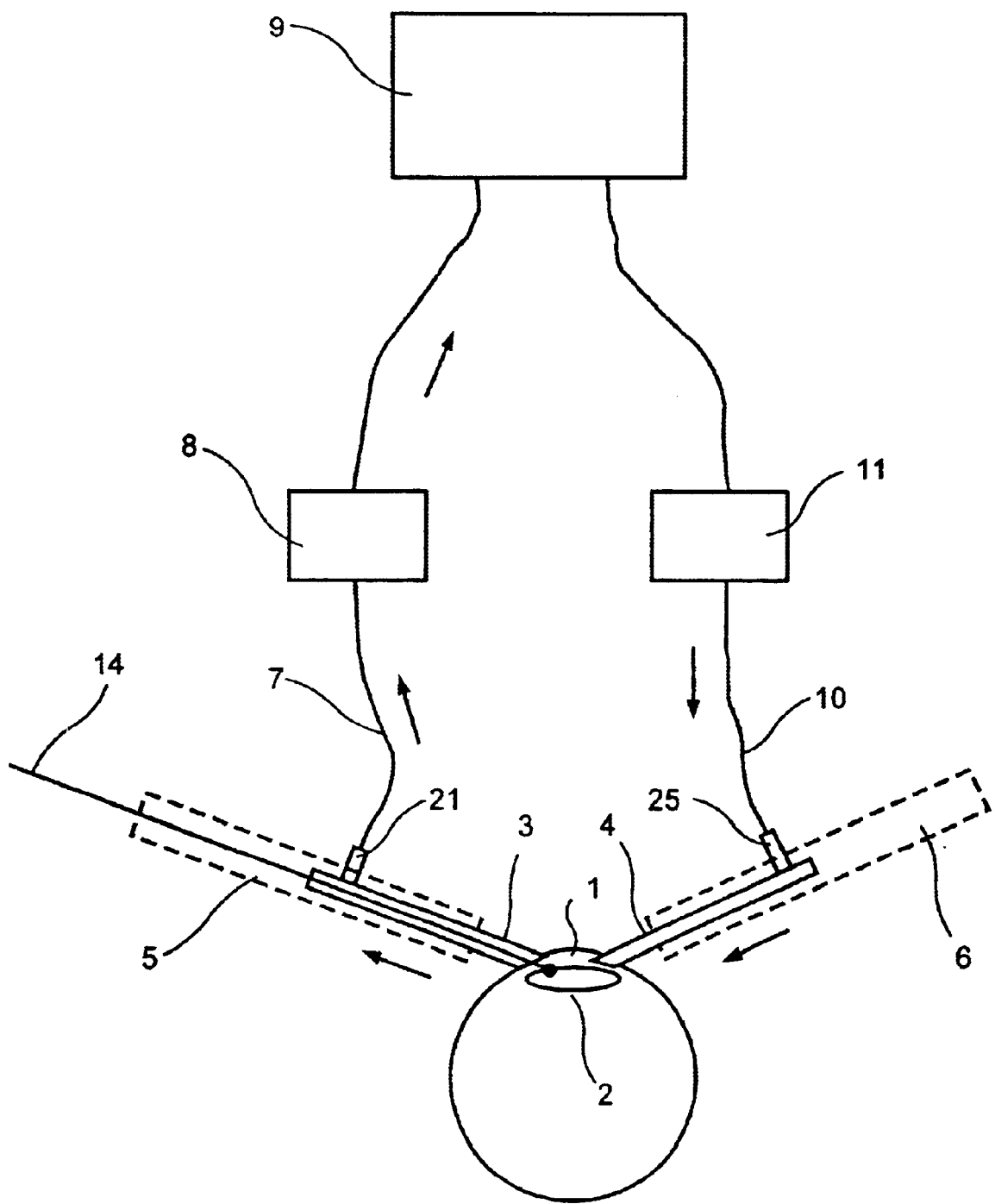
FIG. 1 a schematic view of a first embodiment example.

In a first embodiment example according to FIG. 1, an eye lens 2 which is covered by a cornea 1 and which is to be extracted by means of the arrangement according to the invention is shown schematically. For this purpose, a cannula 3 and a cannula 4 are inserted through incisions in the cornea 1 from approximately opposite directions into the anterior chamber of the eye as far as the eye lens 2. Further, it will be seen from FIG. 1 that cannula 3 is associated with a handpiece 5 and cannula 4 is associated with handpiece 6.

Further, FIG. 1 shows that the handpiece 5 and, along with it, the cannula 3 is connected to an irrigating-aspirating unit 9 via a feed line 7, for example, a flexible tube, and via a suction pump 8. Analogously, the handpiece 6, and accordingly the supply cannula 4, is connected via a feed line 10 to an infusion pump 11 which is coupled in turn with the irrigating-aspirating unit 9.

Figure 2:
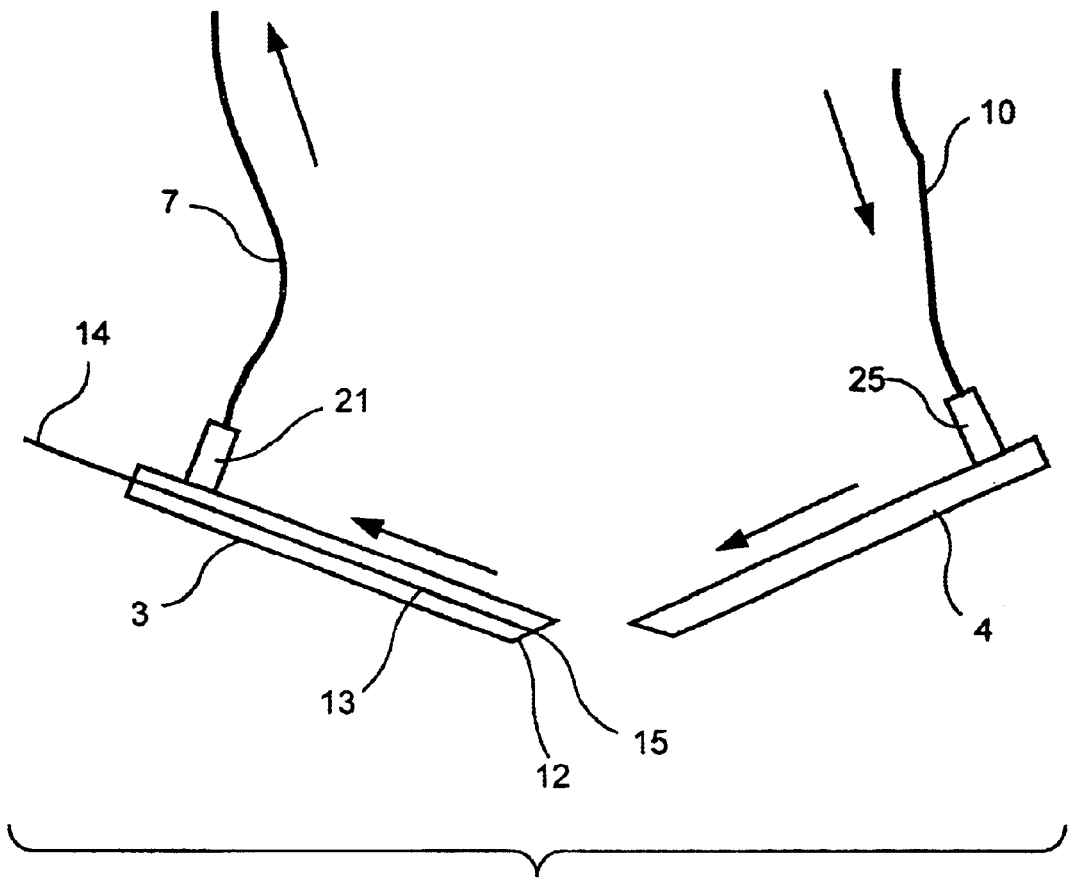
FIG. 2 an enlarged section from FIG. 1.

As is shown in a magnified view in FIG. 2, the cannula 3 has an outlet opening 12 which is inclined at an angle $\alpha \neq 90°$ in the suction direction. A fiber tip 13 is enclosed by the outlet opening 12 and is connected, via coupling optics (not shown in the drawing) provided inside the handpiece 5, to a light-conducting fiber 14 which is connected in turn to a laser unit (also not shown in the drawing). This laser unit preferably contains an Er:YAG laser as radiation source. The laser radiation is guided from the laser source via the light-conducting fiber 14 and is provided at the light exit face 15 of the fiber tip 13 for radiating into the core material.

The light exit face 15 can be oriented at right angles to the suction direction; however, it is also possible for the light exit strip 15 to be constructed at an inclination to the suction direction.

At the start of the cataract extraction, the inclined outlet opening 12 of the cannula 3 is initially inserted into the anterior chamber of the eye and the irrigating-aspirating unit 9 is controlled, so that the suction pump 8, the infusion pump 11 and the laser unit are put into operation. Laser energy is radiated into the core material and comminutes the latter by portions. The fragments are sucked out through the outlet opening 13, the suction cannula 3 and the feed line 7.

In order to prevent a reduction in the intraocular pressure when sucking the liquid and lens fragments out of the anterior chamber, a rinsing liquid which has been introduced 4 from the opposite side in the meantime is provided by the irrigating-aspirating unit 9 via the infusion pump 11 and the feed line 10. The pressure is maintained within the anterior chamber by supplying liquid.

Due to the local separation of the cannula 3 and cannula 4 according to the invention, it is possible to construct both cannulas 3, 4 with a diameter of a maximum of 1.3 mm. Since there is a quasi-nonthermal process taking place with the radiation of laser energy, in contrast to ultrasonic phacoemulsification, the irrigating liquid need not be used for cooling and can accordingly be supplied by the cannula 3 in a spatially separate manner.

In a second embodiment example which will be described in the following with reference to FIG. 3, a switchable directional valve 16 is arranged in the feed lines between the handpieces 5 and 6 and the irrigating-aspirating unit 9. On one hand, this directional valve 16 is connected with the feed line 10 coming from the infusion pump 11 and with the feed line 7 leading to the suction pump 8. On the other hand, the directional valve 16 has two outputs 17 and 18 and two inputs 19 and 20.

Figure 3:
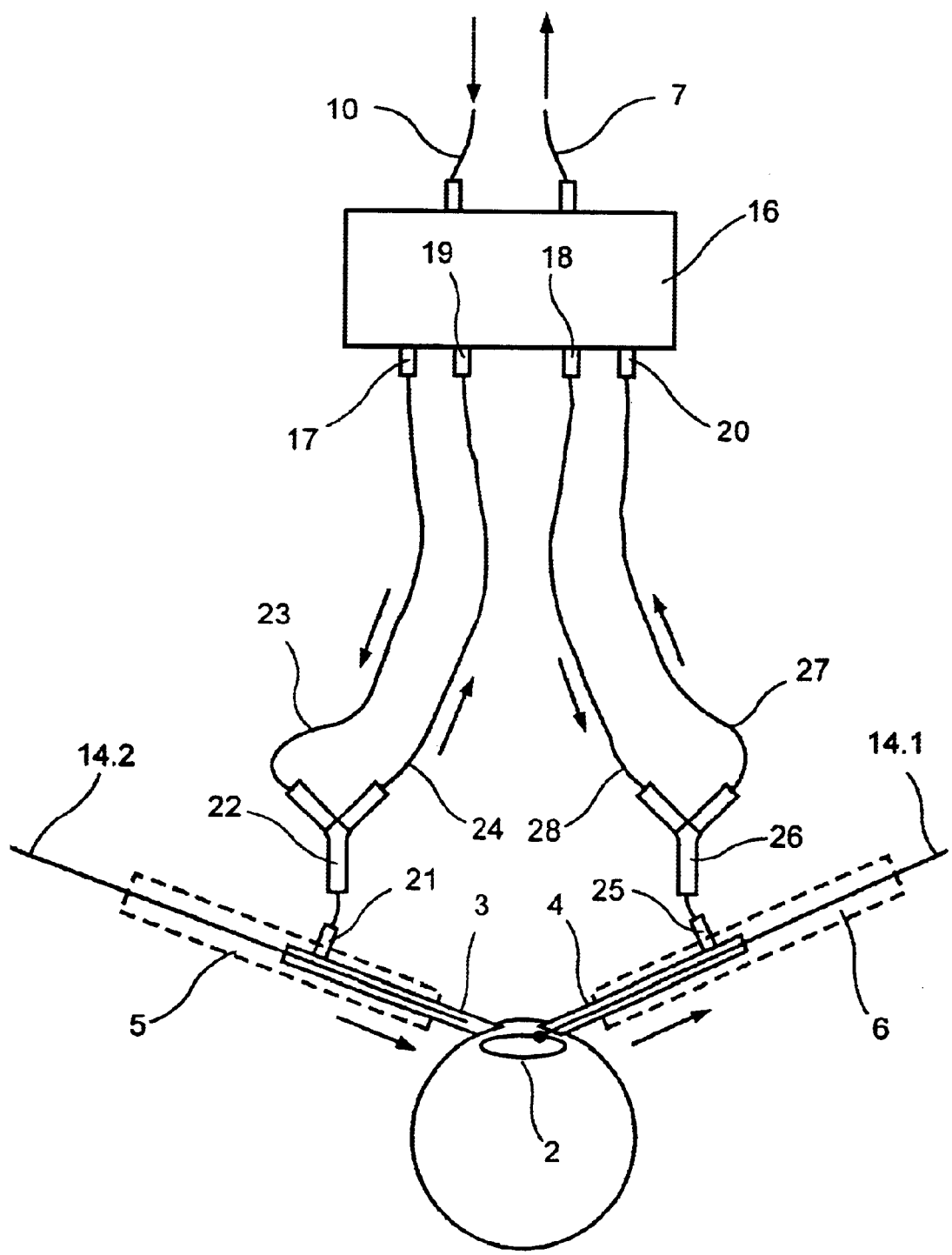
FIG. 3 a schematic view of a second embodiment example.

As is further shown in FIG. 3, the handpiece 5 is connected with the output 17 and also with the input 19 similar to the handpiece 6 connected with the output 18 and the input 20. The connection 21 at the handpiece 5 branches off via branch 22 into two line paths, one of which is connected with the output 17 via a feed line 23, while a second is connected with the input 19 via a feed line 24.

In the same way, the connection 25 of the handpiece 6 branches, via a branch 26, into two line paths, one of which is connected to the input 20 via a feed line 27, while a second is connected to the output 18 via a feed line 28.

The directional valve 16 is connected with a foot switch (not shown in the drawing) by means of which the directional valve 16 can be switched in such a way that the flow from feed line 10 flows selectively to output 17 or output 18 and the feed line 7 for suction is selectively connected to input 19 or input 20.

When a first valve position of these two possible valve positions is selected and the foot switch is correspondingly actuated, the output 17 is connected, via feed line 23, to the handpiece 5 and rinsing liquid is supplied via the cannula 3. At the same time, the handpiece 6 is connected to input 20 via branch 26 and feed line 27 in this first valve position, wherein the ablated core material is sucked out through the cannula 4 and reaches the suction pump 8 via directional valve 16 and feed line 7. Laser energy is supplied through a fiber tip 14.1 inside the cannula 4.

When the operator intends to work with the core material proceeding from the opposite side of the eye lens, it is possible to actuate the foot switch and accordingly move the directional valve 16 into the second valve position in which the through-flow connection between feed line 10 and output 17 is severed and, in its place, a connection is produced between feed line 10 and output 18. The through-flow connection between input 20 and feed line 7 is likewise interrupted and, in its place, a connection is made between input 19 and feed line 7.

The rinsing liquid is now supplied by the infusion pump via feed line 10 through the directional valve 16 and its output 18, through feed line 28 and branch 26 into the handpiece 6 and into the cannula 4 which is integrated in handpiece 6, and from the distal end of the latter to the treatment site.

At the same time, aspiration is carried out with handpiece 5, since its cannula 3 is connected with suction pump 8 via branch 22, feed line 24, input 19, directional valve 16 and feed line 7.

In this connection, a fiber tip is also associated with handpiece 5 for supplying laser energy and is arranged inside the cannula 3. This fiber tip can be connected with the laser source via a light-conducting fiber 14.2, for example. Accordingly, energy can also be introduced into the core material via handpiece 5, the core material can be ablated and sucked out through the cannula 3 as was described.

When the fiber tip is temporarily not in use in the respective handpiece 5, 6, it can be retracted into the respective cannula 3, 4 according to an option of the invention, as is indicated by way of example in cannula 3. This does not impede the introduction of rinsing liquid.

In some case it is advantageous when the branches 22, 26 are outfitted with non-return valves which prevent liquid that has already been sucked out from returning to the eye unintentionally when switching the directional valve 16 or immediately after switching. In the simplest case, the non-return valves are constructed as freely movable flaps which contact valve seats in a sealing manner in the event of backed up liquid or reflux and accordingly prevent the reflux.

In preferred constructional variants, one of the two handpieces or, in some cases, both handpieces, can be coupled with mechanical auxiliary instruments, for example, to fix, mobilize or divide the lens or lens parts. Accordingly, for this purpose, no separate auxiliary instruments need be inserted into the anterior chamber; rather, the required handling can be carried out with the handpieces which are outfitted in this manner.

FIG. 4 shows a selection of auxiliary instruments. For example, FIG. 4a) shows loops for holding, FIG. 4b) shows hooks for holding, and FIG. 4c) shows auxiliary instruments for gripping. Further, auxiliary instruments can be provided for cutting (scissors) and/or for splitting the core material (knives), for protection (protective shield), or also for illumination (fiber ends). Auxiliary instruments of this kind are known from the prior art and therefore need not be described in more detail herein.

This technique of phacoemulsification which is applicable with the instrument according to the invention has the advantageous result that the incisions in the cornea can be made substantially smaller than in the prior art. In this way, fewer losses of aqueous humor and rinsing solution are achieved during the operation, which, apart from the reduced requirement for rinsing solution, results in a reduced liquid volume and accordingly in gentle treatment of the tissue surfaces of the anterior chamber, especially the endothelial layer of the cornea. Moreover, because of the small incisions, there is a reduced risk of astigmatism being induced by the operation. Faster postoperative visual rehabilitation is also possible with incisions of this size.

The construction of the medical instrument for laser phacoemulsification with two handpieces according to the invention enables bimanual phaco-techniques which, apart form the above-mentioned advantages, also allows the operator greater flexibility in intraoperative handling. Using the emulsification principle which can be carried out with this instrument, the operator can remove the cataract through substantially smaller incisions in the cornea than was possible in the prior art. The lens can accordingly be emulsified and aspirated while in the capsular bag and it is no longer necessary to open the capsular bag through capsulorhexis.

As was shown in the preceding, it is possible by means of this handpiece to carry out the operative steps at the eye with substantially smaller incisions in the cornea than was possible using handpieces previously known from the prior art. Accordingly, this handpiece can be advantageously utilized in connection with medical operative procedures in which elastic material is introduced beneath the cornea for purposes of forming intraocular lenses (IOL). The prerequisite for these methods of injectable intraocular lenses is phacoemulsification with very small incisions.

While the foregoing description and drawings represent the present invention, it will be obvious to those skilled in the art that various changes may be made therein without departing from the true spirit and scope of the present.

What is claimed is:

1. A medical instrument for phacoemulsification with which the biological tissue of a lens of the eye is ablated by the introduction of energy, the ablated product is sucked out through an incision in the cornea, and the intraocular pressure is maintained by supplying an irrigating liquid, comprising:

two cannulas for sucking out the ablated lens material and for supplying the irrigating liquid;

at least one device being provided for the introduction of energy through laser radiation;

said two cannulas being enclosed by separate handpieces which are movable relative to one another;

one of said handpieces with the first cannula communicating with a suction device via a feed line;

the other of said handpieces with the second cannula communicating with a supply device for the irrigating liquid via another feed line, and wherein each of the two handpieces and accordingly each of the two cannulas can be connected to the suction device and to the supply device via the feed lines, wherein there is provided in the feed lines between the cannulas and the suction device and supply device a switchable directional valve by which, in a first valve position, the first cannula is connected with the suction device and the second cannula is connected with the supply device and, in a second valve position, the second cannula is connected with the suction device and the first cannula is connected with the supply device, and wherein the first cannula is connected with the directional valve via two feed lines, the second cannula is connected with the directional valve via two other feed lines, and the directional valve is connected with the suction device via a feed line and with the supply device via another feed line, wherein a feed line connected with the first cannula or a feed line connected with the second cannula can be connected to the suction device via a feed line or connected to the supply device via a feed line selectively by the directional valve.

2. The medical instrument according to claim 1, wherein each cannula has a connection, wherein the connection of the first cannula is connected with the two feed lines via a branch and the connection of the second cannula is connected with both feed lines via a branch.

3. The medical instrument according to claim 2, wherein the branches are integrated in the respective handpiece.

4. The medical instrument according to claim 1, wherein the directional valve is connected with a foot switch and can be switched selectively into the two valve positions by actuating this foot switch.

5. The medical instrument according to claim 1, wherein each cannula is assigned to one of the separate handpieces, wherein the two handpieces are movable relative to one another and are designed ergonomically to be used by the operator with both hands.

6. The medical instrument according to claim 1, wherein at least one of the handpieces comprises, apart from the cannula, the device for introducing energy through laser radiation, wherein this device is preferably constructed as a fiber tip.

7. The medical instrument according to claim 1, wherein a fiber tip is arranged inside the cannula or the cannula at least partially, wherein the light exit face of the fiber tip is enclosed by the outlet opening of the respective cannula.

8. The medical instrument according to claim 1, wherein a fiber tip is displaceable within the cannulas in the direction of flow.

9. The medical instrument according to claim 1, wherein the first cannula and the second cannula have the same diameter in the range of magnitude of 0.8 mm to 1.3 mm.

10. The medical instrument according to claim 1, wherein the first cannula and the second cannula have different diameters within the range of 0.8 mm to 1.3 mm, wherein the first cannula is larger than the second cannula.

11. The medical instrument according to claim 1, wherein an infusion pump is provided as supply device and a suction pump is provided as suction device, each device being connected with a controllable irrigating-aspirating unit.

12. The medical instrument according to claim 1, wherein an Er:YAG laser is provided as energy source.

13. The medical instrument according to claim 1, wherein the handpiece with the first cannula and/or the handpiece with the second cannula are/is outfitted with auxiliary instruments for holding, gripping, turning, pushing, cutting, splitting, protecting or illuminating the tissue at the treatment site.

14. The medical instrument according to claim 1, wherein auxiliary instruments can be connected with the handpieces selectively and alternately by an attaching mechanism.

15. The medical instrument according to claim 1, wherein auxiliary instruments are arranged at the handpieces so as to be retractable.

16. The medical instrument according to claim 1, wherein auxiliary instruments are arranged at the handpieces so as to be displaceable on a guide path.

17. The medical instrument according to claim 1, wherein a device for cleaning the cannulas, the feed lines and/or the branches is provided in at least one of the two handpieces and serves to eliminate clogging when needed.

18. The medical instrument according to claim 1, wherein a device for cleaning is constructed as a spiral which is displaceable in the direction of flow.

19. The medical instrument according to claim 1, wherein at least one of the two handpieces is outfitted with a coupling mechanism for a device for supplying substances for injectable intraocular lenses.

20. The medical instrument according to claim 1, wherein connections are provided in the first cannula and/or in the second cannula, which connections communicate, via the coupling mechanism, with a device for supplying substances for injectable intraocular lenses.

* * * * *